(12) United States Patent
Haininger

(10) Patent No.: US 8,486,072 B2
(45) Date of Patent: Jul. 16, 2013

(54) IMPLANT FOR TREATING A PROXIMAL FRACTURE OF THE HUMERUS

(75) Inventor: Christian Haininger, Bad Voslau (AT)

(73) Assignees: Christian Haininger, Bad Vöslau (AT); Arthrex, Inc., Naples, FL (US)

( * ) Notice: Subject to any disclaimer, the term of this patent is extended or adjusted under 35 U.S.C. 154(b) by 137 days.

(21) Appl. No.: 13/063,157

(22) PCT Filed: Sep. 16, 2009

(86) PCT No.: PCT/AT2009/000358
§ 371 (c)(1),
(2), (4) Date: Apr. 21, 2011

(87) PCT Pub. No.: WO2010/031098
PCT Pub. Date: Mar. 25, 2010

(65) Prior Publication Data
US 2011/0190769 A1    Aug. 4, 2011

(30) Foreign Application Priority Data
Sep. 16, 2008   (AT) ................................ A 1444/2008

(51) Int. Cl.
*A61B 17/58* (2006.01)
(52) U.S. Cl.
USPC .......................................................... 606/64
(58) Field of Classification Search
USPC .................................. 606/62–68, 96–99, 104
See application file for complete search history.

(56) References Cited

U.S. PATENT DOCUMENTS

| | | | | |
|---|---|---|---|---|
| 5,658,287 A * | 8/1997 | Hofmann et al. | ............... | 606/63 |
| 5,665,086 A * | 9/1997 | Itoman et al. | .................... | 606/64 |
| 5,766,174 A | 6/1998 | Perry | | |
| 7,179,259 B1 | 2/2007 | Gibbs | | |
| 7,763,021 B2 * | 7/2010 | Cole et al. | ........................ | 606/64 |

FOREIGN PATENT DOCUMENTS

| | | | | |
|---|---|---|---|---|
| DE | 9115200 | | 2/1992 | |
| DE | 19912696 | * | 10/2000 | ..................... 606/64 |
| DE | 19912696 A1 | | 10/2000 | |
| EP | 1398000 | * | 3/2004 | ..................... 606/64 |
| EP | 1685803 | | 8/2006 | |
| WO | WO 97/39693 | | 10/1997 | |
| WO | WO 2009/021624 | | 2/2009 | |

OTHER PUBLICATIONS

International Search Report from PCT/AT2009/000358, dated Apr. 9, 2010.

* cited by examiner

*Primary Examiner* — Pedro Philogene
(74) *Attorney, Agent, or Firm* — Dickstein Shapiro LLP

(57) ABSTRACT

An intramedullary pin for treating a proximal fracture of the humerus, the pin having at least one distal and at least one proximal part which can be moved in relation to one another in order to modify the length of the implant and which have co-operating guide surfaces. The proximal and the distal part have co-operating stops for limiting the axial relative movement, the proximal part and distal part being capable of relatively free movement within the delimitations defined by the stops and each being provided with at least one transverse bore for receiving and/or fastening fixing means. The implant is also provided with a mechanism for locking the relative movement of the two parts about the implant axis.

16 Claims, 10 Drawing Sheets

IMPLANT FOR TREATING A PROXIMAL FRACTURE OF THE HUMERUS

RELATED APPLICATIONS

This application is a national stage filing under 35 U.S.C. §371 of international application PCT/AT2009/000358, entitled "IMPLANT, IN PARTICULAR INTRAMEDULLARY PIN FOR TREATING A PROXIMAL FRACTURE OF THE HUMERUS," filed on Sep. 16, 2009, which claims priority to Austrian Patent Application No. A 1444/2008, filed on Sep. 16, 2008.

BACKGROUND OF THE INVENTION

The invention relates to an implant, in particular an intramedullary pin for treating a proximal fracture of the humerus, said pin having at least one distal and at least one proximal part, which are arranged so as to be displaceable axially in relation to one another to modify the length of the implant and which have guide surfaces cooperating with each other.

The fracture of the proximal portion of the humerus, i.e. the breaking of the head of the upper arm into two or more parts and/or of the adjoining upper arm shaft, is still a problem of fracture care which has not been finally solved in accident surgery. This is also shown by the plurality of different procedures, operative possibilities and implants which have been discussed and recommended for years in this context.

The shoulder is the most movable joint of the human body. In order to make this possible, the joint socket of the shoulder joint is scarcely developed. The guidance during movement and the stability are only achieved by the joint capsules, ligaments, musculature and tendons, which are attached directly to the upper arm head or in the immediate proximity.

In the case of a breakage of the upper arm head into two, but generally into several parts, typically the following situation occurs: The breakage zone between the upper arm head and upper arm shaft (subcapital fracture zone) is very unstable, the fragments are often displaced considerably. The parts of the upper arm head to which tendons are attached (tubercles), are not only dislocated by the trauma but also by the traction of the tendons. The piece bearing joint surfaces is tilted, owing to the lack of support. If the adjoining part of the upper arm shaft is also affected, a displacement of fragments can also take place here. In any case, however, a further increase to the instability occurs. In addition to this is the fact that the tuberculum majus, to which the essential tendons are attached for the movement of the upper arm, and which additionally offers an important support of the piece bearing the joint surface, almost always breaks up into several, partly very small pieces.

Furthermore, the fracture of the upper arm head is typically an injury which occurs primarily in older people. As a result of the poorer quality of the bone, implants often only find an insufficient hold here. A complete immobilization of the shoulder joint in a bandage is not possible, therefore after operative care, tractive, bending and shearing forces still also occur onto the subcapital fracture zone and on parts of the upper arm head or upper arm shaft.

In the weeks after the trauma, when the patient starts to move the arm again, a "collapsing" of the subcapital fracture zone always occurs. This is the prerequisite that the fracture is growing together. Only thereby are a rapid fracture healing and the avoidance of a pseudoarthrosis possible. Tractive forces of the tendons (rotator cuff) continue to act on parts of the upper arm head. If screws of implants do not find a good hold in the bone or if not all the pieces of bone are fixed by the implants in a stable manner with regard to movement, the danger exists that in the weeks after the operation, when musculature is used again, a secondary dislocation of fracture parts and/or osteosynthesis material occurs.

The osteosynthesis should be stable with regard to movement, in order to be able to begin the physical therapy as early as possible without the risk of secondary dislocation. In an older person namely a lengthy immobilization of the shoulder joint is connected with a shrinkage of the joint capsule and hence an often painful restriction to movement.

A removal of the implant should not be ordinarily necessary, because damage to the soft tissue can occur through a further operation. Furthermore, the rehabilitation is impaired in a negative manner by the necessary renewed postoperative protection.

The implants which are currently common, which are used for the care of these fractures, can be classified into two groups:

Semirigid implants, which primarily have the aim of fixing the subcapital fracture zone in the repositioned state, and which at the same time permit a collapsing of the fracture. The remaining fragments of the upper arm head are fixed here by screws. The advantages of this method lie in the good osseous healing of the subcapital fracture, because through the collapsing a certain compression occurs, which promotes the healing of the fracture. It is found to be disadvantageous that the screwed tubercles can still move easily in the first weeks. This is on the one hand because it is not possible to fix all the fragments by means of screws, and on the other hand because the screws find only a very little hold in the soft bone structure of the upper arm head and a screwing through of the opposite hard corticalis bearing the joint surface must be avoided, because the screw tips would then project into the joint. In the case of a dislocation of the tuberculum majus, however, the support of the part bearing the joint surface is also absent, whereby a tilting of the entire upper arm head is possible in the first days and weeks after the operation. Therefore, fractures which are treated by these implants must often be fixed for a longer time by a bandage, which results in a restriction to the movement of the shoulder joint. Fractures which additionally also extend into the upper arm shaft can generally not be treated with these implants at all. Included among the semirigid implants are:

Spongiosa Screws, Drill Wires

The screws or drill wires can be positioned well in an ideal position, i.e. in a diverging position and at right angles onto the acting forces which are to be expected.

However, they often only find a poor hold in the bone spongiosa of the upper arm head. As a result of the poor anchoring possibilities, often a slipping of the fragments and of the screws or wires occurs upon movements in the shoulder joint. On the collapsing of the subcapital fracture, the implants can "slip back" in a lateral direction, whereby the fragment bearing joint surfaces can tilt again.

Drill Wires And Humerus Block

The block prevents the slipping back of the drill wires. On collapsing, the perforating of the drill wires through the joint surface into the joint can occur. This implant must always be removed after a few weeks in a second operation. The tubercles are provided with screws, for which the disadvantages described above apply.

Intramedullary Wires

Often, it is not possible to reposition the fracture or to fix the repositioned result. Here, also, the slipping of the wires can easily occur, either proximally through the joint surface or also in a distal direction. Here, also, the tubercles are provided with screws.

Helix Wire

The helix wire can compensate well for the collapsing of the subcapital fracture zone; perforation through the joint surface occurs very rarely. However, the same disadvantages apply as in the case of the intramedullary wires; with this implant, it is also not often possible to fix the rotation.

Rigid Implants

With these implants, generally a good reposition result can be achieved. The fixing of the tubercles is also generally possible to a better extent. On the one hand, because the fragments of the tuberculum majus are fixed through the surface of the plate, and on the other hand because the screws are not only fixed in the spongy bone, but also find a hold in the implant (plate, pin). However, these implants can not compensate for the movements occurring postoperatively. In the region of the subcapital fracture zone, a compression is not possible, therefore poor osseous healing and pseudoarthoses can occur here. If the arm is moved before the osseous healing, parts of the implants which are in fact fixed on the upper arm shaft can perforate through the joint surface on collapsing of the fracture or can cause the fracture pieces of the upper arm head to slip again.

Plate

The screws of the plate do in fact fine a good hold on the upper arm shaft, but little hold in the bone of the upper arm head. On postoperative moving, the dislocation or pulling out of these screws often occurs, whereby the reposition result is lost and the plate has to be removed again. Furthermore, through the areal compression of the plate onto the bone, the blood flow of the periosteum and hence the healing of the bone is disturbed.

Angle-stable Plate

The screws are fixed in the plate in an angle-stable manner and can not slip. However, they nevertheless do not find a good hold in the spongy bone. Especially the fragment of the upper arm head bearing joint surfaces can "detach" itself from the spongiosa screws of the plate and can tilt again. With a good osseointegration both into the upper arm head and also into the upper arm shaft, with a lack of subcapital healing a breakage of the plate can occur as a result of the movements in this zone. For the implantation of plates, a relatively large skin incision is necessary, with the disadvantages of soft tissue damage connected therewith.

Humerus Pin

As an intramedullary force carrier, the pin compensates well for all the forces which occur, and also a breakage of the pin never occurs. The surgical access is small, protects the soft tissues and the fracture zone is not additionally traumatized. However, the pin is fixed both in the upper arm head and also on the upper arm shaft and does not permit any collapsing in the subcapital fracture region. It can therefore happen that on collapsing of the subcapital fracture zone, the upper arm head or parts thereof are displaced over the pin in a caudal direction and therefore the pin or the locking screws project over the bone. If the screws can fix the upper arm head well, the pin prevents a sliding together of the subcapital fracture zone. Therefore, the compression of the fracture surfaces is absent and an absent fracture healing with persistent movement pain can occur.

Humerus Pin In Combination With Angle-Stable Plates (WO 2009/021624 A1)

The disadvantages of the intramedullary pin (risk of dislocation of the tuberculum minus, few screws for fixing the fragment bearing the joint surface) are minimized by the use of a small plate which fixes the tuberculum majus and is fixed on the pin by means of a rigid connection. The screws in the upper arm head are fixed in the plate in an angle-stable manner. The advantage is, without doubt, that the tuberculum majus is fixed in a distinctly better manner.

However, it remains as a disadvantage that, as in all the screws which are used, a holding of the screw thread in the opposite thin corticalis is only possible to a limited extent, so that a dislocation of the joint surface bearing fracture piece is still possible. As the plate is rigidly connected with the pin, on collapsing of the fracture in the subcapital zone, in the same way as with the humerus pin, a dislocation of the entire pin/plate construction can also occur in a cranial direction. By the relative higher placement of the plate, the "impingement syndrome" can occur here or, in the worse case, a perforation of the pin/plate construction through the upper arm head in a cranial direction.

At times, irrespective of the result of the operation, it can become necessary to subsequently replace an operated humerus head by a prosthesis. According to the prior art, to do this, an implant which may be present, which serves for the reposition and fixing of a humerus fracture, must be removed, which frequently proves to be difficult when the implant has grown securely into the bone. A corresponding operation entails an extensive impairment to the bone here and a considerable irritation to the soft tissue, so that the successful insertion of an implant is made difficult. It would therefore be desirable to be able to use a part of an inserted implant as a shaft for a prosthesis.

SUMMARY OF THE INVENTION

It is an object of the present invention to further develop an implant of the type named in the introduction to the effect that as optimum a combination as possible of the advantages of the implants represented above is successful, wherein the disadvantages of the individual variants are to be avoided. The fracture pieces of the upper arm head are to be fixed after reposition in the sense of a proximal locking on the implant. The joint surface bearing fragment is to be fixed or respectively supported by means of screws, drill wires or pins. These must not exceed the opposite bone boundary (i.e. the joint surface), but should support this joint surface bearing piece of bone both against pressure and also against tangential shearing forces.

In addition, the tubercles are to be fixed in their anatomical position and to be held until osseous healing. Owing to the often poor bone quality, the fixing must be anchored in an angle-stable manner on the implant, in order to avoid a secondary dislocation.

In fractures of the tuberculum majus into several parts, an areal fixing should be achieved.

In order to fix the rotation, a distal locking is necessary in a typical manner. If a fracture of the upper arm shaft is also present, various pin lengths are necessary, in order to make possible a sufficient intramedullary splinting. If displaced fracture pieces are present on the upper arm shaft, these are also to be fixed by means of screws at the corresponding height on the pin. In the region of the subcapital fracture zone, the "collapsing" of the fracture zone is to be possible over a predetermined maximum distance in the weeks after the operation, without the rotation stability or the fixing of the remaining fracture pieces being impaired.

The surgical trauma should be kept as little as possible. A removal of the implant should not be compulsorily necessary.

Furthermore, it is an object of the present invention to further develop an implant of the type named in the introduction to the effect that a later use of a part of the implant as a prosthesis shaft becomes possible.

To solve these problems, the implant of the type named in the introduction is further developed according to the invention to the effect that the proximal and the distal part have stops cooperating with each other for limiting the axial relative displacement, that the proximal and the distal part are freely displaceable relative to each other within the delimitations defined by the stops, that the proximal and the distal part are each provided with at least one transverse bore for receiving and/or fastening fixing means and that means are provided for locking the relative rotation of the two parts about the implant axis. Through the fact that the proximal and the distal parts have stops cooperating with each other for limiting the axial relative displacement, and that the proximal and the distal parts are freely displaceable relative to each other within the delimitations defined by the stops, a collapsing of the subcapital fracture zone is made possible within the limits defined by the stops. With a collapsing of the subcapital fracture zone during the healing process, the proximal and the distal parts of the implant move towards each other, so that an emergence of the intramedullary pin or of fixing means from the proximal end of the humerus is avoided and an optimum maintaining of the reposition result is achieved. The axial displaceability is limited here by stops in both directions, so that a collapsing of the subcapital fracture zone can only take place within the predetermined limits. Within these limits, the parts are, however, freely displaceable, and in particular no separate locking, releasing or adjusting means or suchlike are provided, releasing or adjusting the displaceability if applicable from the exterior.

At the same time, through the fact that the proximal and the distal parts are each provided with at least one transverse bore for receiving and/or fastening fixing means, a fixing of the intramedullary pin in the humerus can be carried out both in the shaft region and also in the head region, with further fracture pieces being able to be fixed in the desired position by means of further screws as with a plate. Through the fact that means are provided for locking the relative twisting of the two parts about the implant axis, it is ensured that with a free displaceability of the proximal and distal parts with respect to each other, the reposition result of a subcapital fracture is not jeopardized.

Advantageously, the implant according to the invention is further developed to the effect that the guide surface of the distal part is constructed on a projecting section thereof, constructed with a reduced diameter, and that the guide surface of the proximal part is constructed on the inner circumference of a hollow section embracing the projecting section of the distal part. This permits a particularly simple and compact type of construction of the implant according to the invention, wherein in a particularly simple manner the distal part dips into the proximal part which is constructed as a sleeve.

Advantageously, the implant according to the invention is further developed to the effect that the guide surface of the sleeve is constructed on a region which is constructed with a reduced internal diameter, whereby the sleeve is constructed in the region of its guide surface and therefore in the region of the mechanical cooperation with the distal part of the implant with an increased wall thickness. Thereby, an increased stability of the entire implant is achieved. Furthermore, due to the region with reduced internal diameter in the sleeve a ring-shaped area is produced, which can serve as a stop for limiting the relative displaceability of the two implant parts.

Advantageously, the invention is further developed in this context in that a stop bolt is provided, which is able to be secured adjustably on or in the free end of the projecting section of the distal part, and that the region of the sleeve which is constructed with a reduced internal diameter forms a ring-shaped projection as a stop surface for the stop bolt. In this way, the possible displacement path of the two parts with respect to each other can be simply adjusted.

In a particularly advantageous manner, the implant according to the invention is further developed to the effect that the distal part has a stop, projecting over the external diameter of the proximal part, for the engagement of a target device. A target device can engage on such a stop with simultaneous fixing of the displaceable proximal part, so that the implant, on insertion into the upper arm, which frequently takes place by driving in, is secured against a relative displacement of the two parts with respect to each other and therefore, after the insertion, the maximum displacement path is available for the desired collapsing of the fracture.

Advantageously, the proximal part has at least two, preferably a plurality of transverse bores intersecting each other, into which bone screws can be introduced, in order to be able to fasten a plurality of fracture pieces on the implant.

In a simple manner, the implant according to the present invention is further developed to the effect that the guide surfaces are constructed so as to be cylindrical in sections, with the construction advantageously being able to be further developed to the effect that the guide surfaces form a cross-section of the implant deviating from a circular cross-section. When the guide surfaces are constructed so as to be cylindrical in sections, the manufacture of the implant can take place in a simple and favourably-priced manner wherein, when the guide surfaces have a cross-section deviating from a circular cross-section, a security against twisting of the two parts with respect to each other is directly achieved. The implant can be further developed here in a preferred manner to the effect that the guide surfaces respectively have at least one groove running in an axial direction, in the shared cross-section of which a rod is received. With such a construction, on the one hand the manufacture can take place at a favourable cost, with the desired security against twisting of the two parts with respect to each other taking place by the rod which is inserted into the grooves.

The security against twisting can preferably also take place in that the proximal or the distal part has an elongated hole extending an in axial direction, in which a bolt, arranged on the other part in a rotationally fixed manner, is guided in an axial direction.

As fixing means, within the framework of the invention, at least one bone screw can be provided. The bone screw(s) can be provided here in transverse bores in the distal part of the implant, in order to fasten the pin in the bone accordingly. In the proximal part, likewise at least one screw can be provided, received in a transverse bore of the implant.

In many cases, however, it is not possible to fix the entire debris zone with individual fixing screws. In order to provide a remedy here, a preferred further development of the implant makes provision that a plate is provided as a fixing means, which is able to be fastened relative to the proximal part of the implant. With the plate, the fragments can be successfully fixed areally.

For fastening the plate, preferably at least one screw is provided, which connects the plate with the proximal part of the implant. The distance between the plate and the implant does not have to be predetermined here, but rather the plate is preferably drawn by the screw towards the implant, until it has reached the bone boundary.

In order to achieve a rotation stability of the plate relative to the implant, in addition to the screw preferably a post is provided for connecting the plate with the implant, the screw head of which has a thread for screwing into the plate and the end of which, facing away from the screw head, is able to be introduced into a transverse bore of the implant. Thereby, a protruding of the plate and hence an impingement syndrome are avoided. The plate is advantageously constructed to the effect that it replicates the curvature of the bone parts which are to be fixed. In addition, it has projecting fillets or points which find a hold on the fragments, whereby on the one hand a secondary dislocation of individual pieces of bone is avoided. On the other hand, an areal bearing of the plate is avoided and hence the blood supply of the bone is not disturbed (periosteal compression).

For the further fixing of the pieces of bone, the construction is preferably made such that the plate has a plurality of through-holes to receive fixing screws and/or posts for the fixing of bone fragments. The posts and/or fixing screws provided for the fixing of bone fragments are advantageously able to be fastened here in an angle-stable manner in the plate.

The fixing screws or respectively bone posts are used particularly for supporting the joint surface bearing part of the upper arm head. The bone posts can be constructed in various lengths and can have a tip which can be anchored well on the opposite corticalis. The posts can have a diverging position relative to each other, can also run partially through the pin, for which bores can be provided in the pin. Thereby, they can support the joint surface bearing part of the upper arm head against all acting forces, independently of the position of the upper arm head to the socket. When the posts are fixed in an angle-stable manner in the plate, they act in identical manner to a locking screw as a means for locking the relative twisting of the two parts about the implant axis.

The invention further relates to a target device for placing bone screws in transverse bores of the implant according to the invention, with the target device being characterized in that the target device has two parts which are displaceable relative to each other in an axial direction, one part of which is able to be connected with the proximal or the distal part of the implant and is able to be displaced together therewith relative to the other part.

Such a target device serves on the one hand in a conventional manner to arrange bores on the bone at suitable sites, in order to fasten corresponding screws in the bone and on the implant. However, through the fact that the target device has two parts which are displaceable relative to each other in an axial direction, one part of which is able to be connected with the proximal or with the distal part of the implant and is able to be displaced together therewith relative to the other part, the target device can, however, be used on the other hand to ensure that on insertion, which usually takes place by driving in, the implant is secured against a relative displacement of the two parts with respect to each other and therefore after the insertion the maximum displacement path is available for the desired collapsing of the fracture. According to the invention, provision is made here that a part of the target device is connected for example with the proximal part of the implant, for example by screws, after which this part is able to be supported on another part of the target device by fixing means so that a displacement of the proximal part towards the distal part of the implant is prevented.

Advantageously, the target device according to the invention is further developed to the effect that the one part of the target device is formed by a sleeve which is able to be slid over the proximal implant part, which sleeve rests on a projection of the distal implant part, and the other part of the target device is formed by a rod arranged in the sleeve, which rod is able to be connected with the proximal implant part preferably by means of a screw connection, wherein in a particularly simple manner the rod carries at its proximal end a screw nut, which rests if applicable indirectly against the sleeve of the target device, so that the part of the target device which is fastened on the proximal part of the implant can be braced against the sleeve, in turn resting against the distal part of the implant, so that a displacement of the two implant parts is ruled out on insertion.

To solve a further problem according to the invention, provision is made to use the distal part of the implant according to the invention as a prosthesis shaft for a humerus head prosthesis. The implant according to the invention is suitable for this in a particular manner, because owing to the two-part construction it is possible in a simple manner to remove the proximal part of the implant and to place a corresponding prosthesis onto the distal part which has remained in the bone. Advantageously, provision is made in this context that the distal part carries a removable intermediate piece. The removable intermediate piece has the guide surfaces here for the free axial displaceability of the distal part to the proximal part and is removed together with the proximal part, so that only a base section of the distal part remains in the bone, which can subsequently be used as a prosthesis shaft. Advantageously, one proceeds here so that after the removal of the proximal part and of the intermediate part, a new intermediate piece is fastened for adjusting the vertical and rotation position and for securing the humerus prosthesis on the distal part of the implant. Such an intermediate piece functions here as an adapter piece, by which a precise positioning of the humerus head prosthesis is possible.

BRIEF DESCRIPTION OF THE DRAWINGS

The invention is explained in further detail below with the aid of an example embodiment which is illustrated in further detail in the drawing, in which.

DETAILED DESCRIPTION OF THE INVENTION

Figure 1:
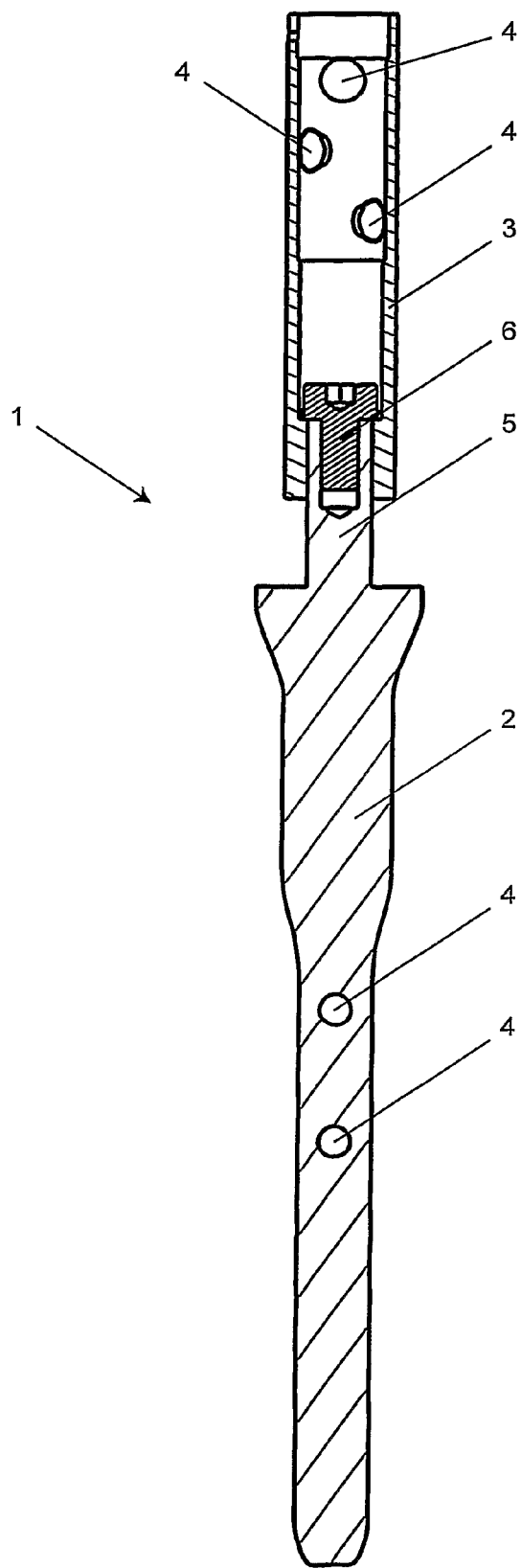
FIG. 1 shows a first embodiment of the implant according to the invention, in which the two parts, which are displaceable with respect to each other, are situated in an extended position.

In FIG. 1, an implant according to the invention is shown by 1, with a distal part 2 and a proximal part 3, which are displaceable relative to each other. The distal part 2 and the proximal part 3 have bores 4 which serve to receive screws, in order to hold the respective implant part in the corresponding bone part so as to be secured with regard to rotation. The screws can be placed here so that they bridge further fracture sites, for example those in the humerus head, and thus fasten fracture pieces of the humerus. The proximal part 3 has at its distal end a region with an increased wall thickness, which forms the guide surface, which in turn cooperates with a guide surface on a post-like extension 5 of the distal region. The relative displacement of the two parts of the implant is therefore guided over these guide surfaces, with a stop being able to be defined for the pulled-apart position by an adjustable screw 6 in the post-like extension 5 of the distal part 2.

Figure 2:
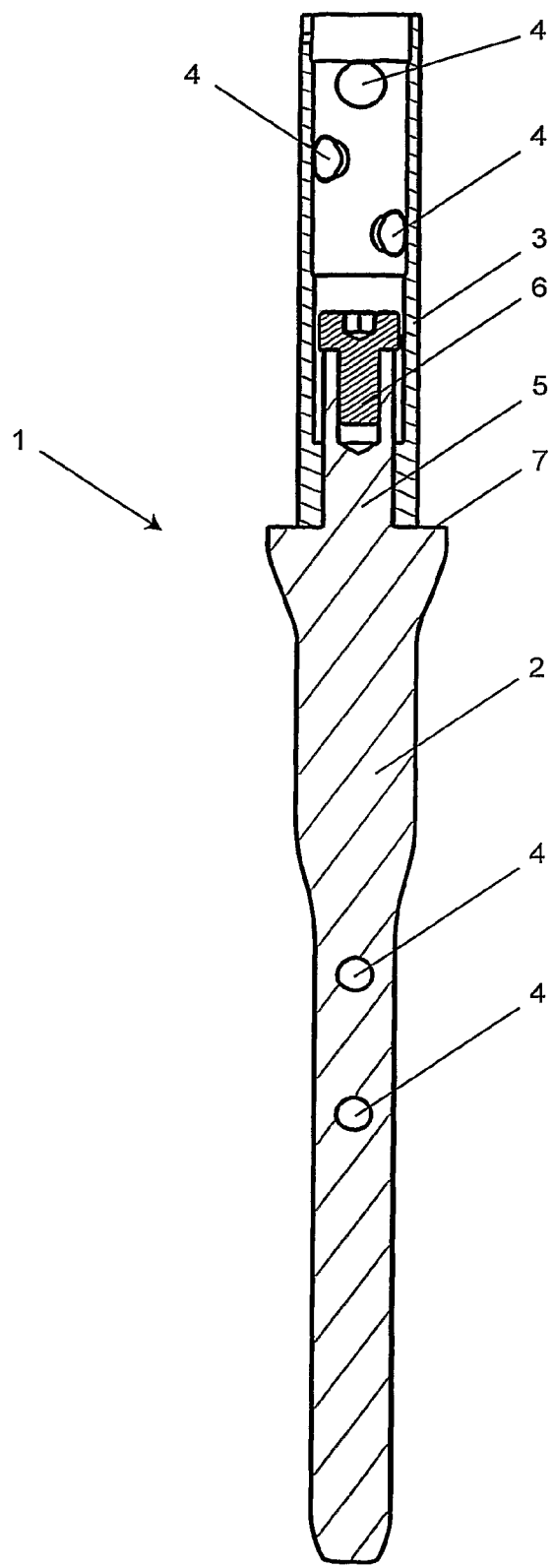
FIG. 2 is an illustration of the same implant, in which the two parts, which are displaceable with respect to each other, are shown in the collapsed position.

In FIG. 2 it can seen that in the collapsed position of the implant, the proximal part 3 comes to lie on a shoulder 7 of the distal part, whereby a stop is defined for the collapsed position.

Figure 3:
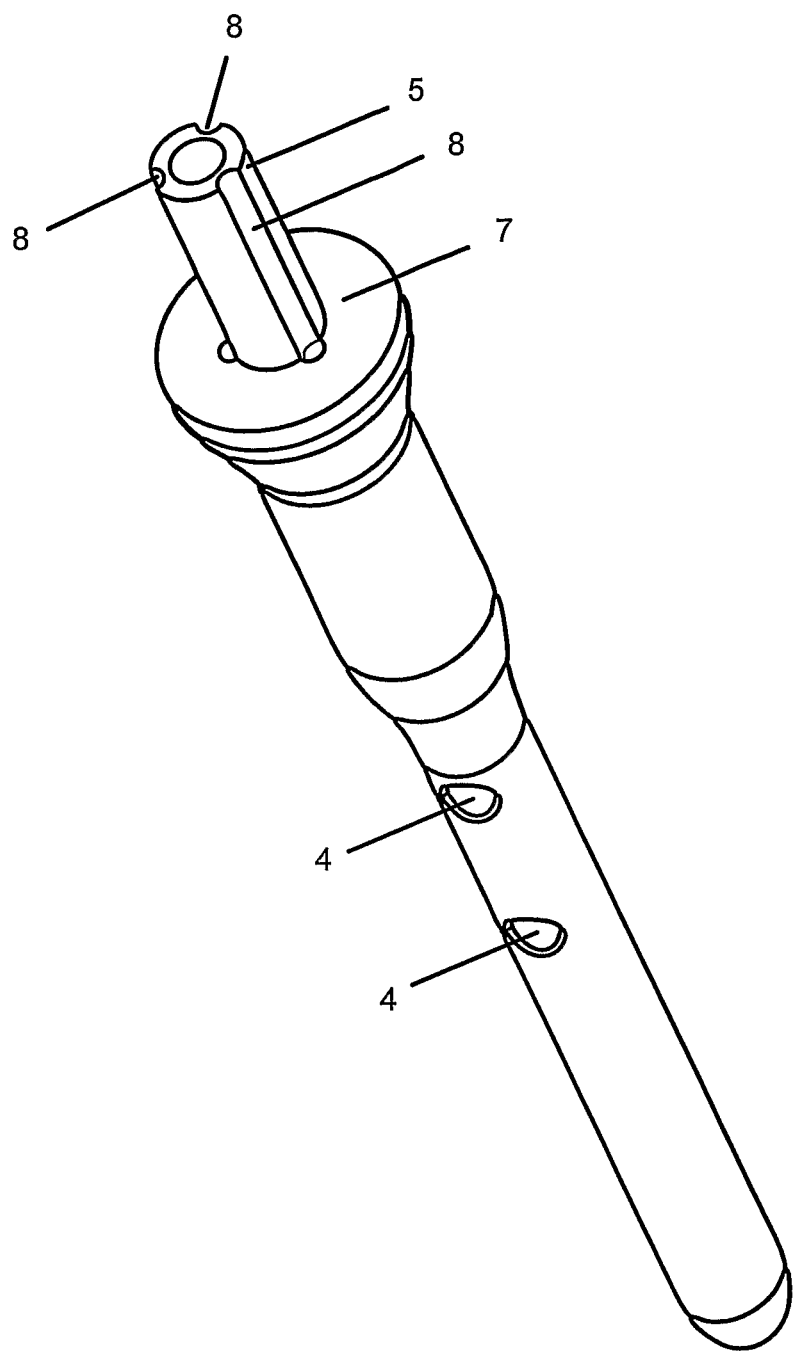
FIG. 3 is a perspective illustration of the distal part of the implant of FIG. 1, in which grooves are provided for the insertion of rods to prevent the rotation of the two displaceable parts with respect to each other about the longitudinal axis of the implant.

In FIG. 3 a number of grooves 8 are illustrated, into which rods can be inserted, which then, when the proximal part of the implant, which is not illustrated, likewise has suitable grooves, represent a security against twisting of the two implant parts with respect to each other.

Figure 4:
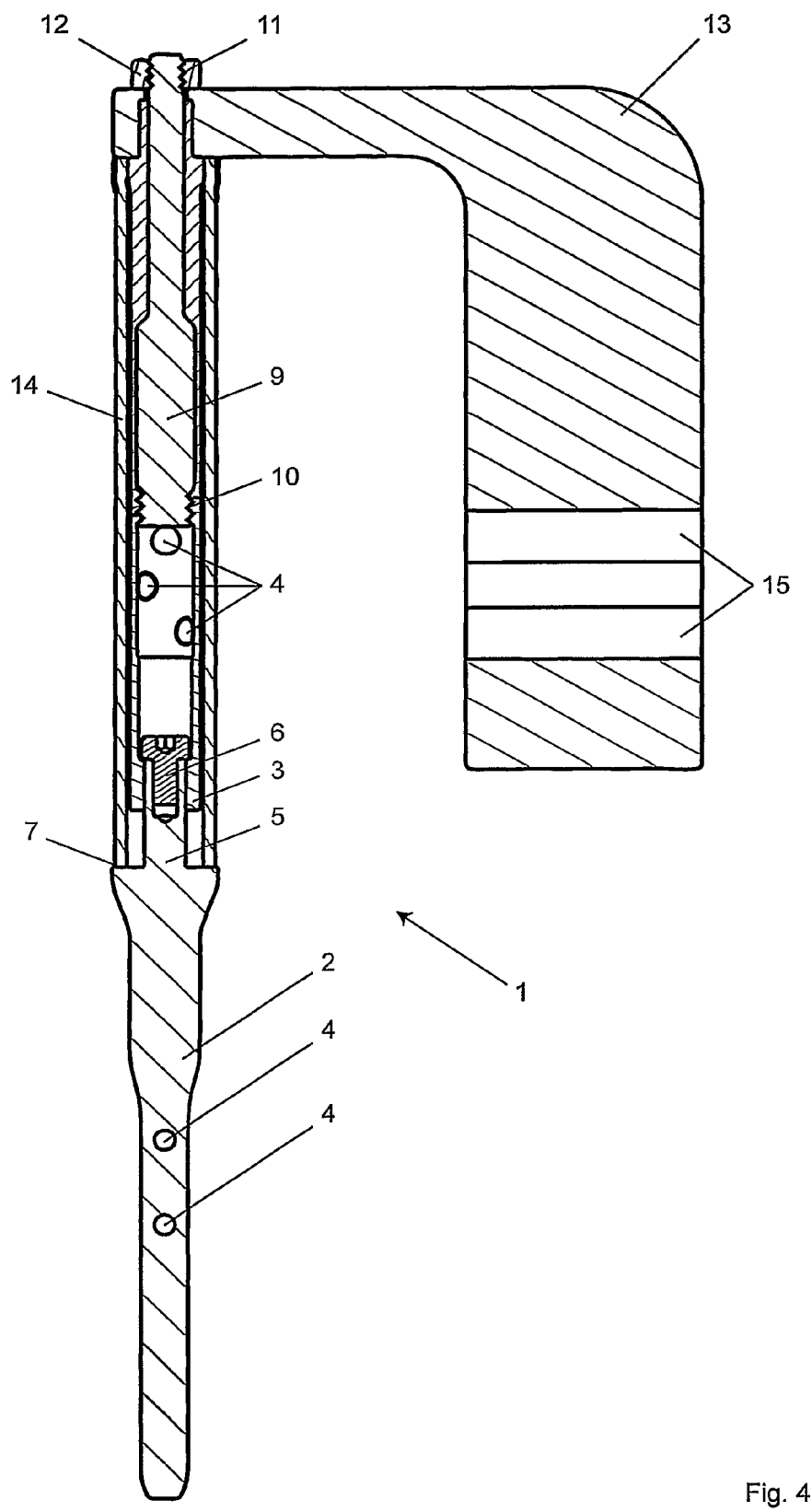
FIG. 4 is an illustration of the implant of FIG. 1 with an applied target device.

In FIG. 4 a post of a target device is designated by 9, which is fastened by means of a thread 10 on the proximal part 3. The post 9 is able to be displaced and braced by means of a thread 11 and a nut 12 for example with interposition of the actual target device 13 against a sleeve 14, so that a fixing of the position of the proximal part 3 to the distal part 2 of the implant exists on insertion. In the target device 13, bores 15 are provided which are in alignment with the bores 4 of the implant, so that a drill which is placed through these bores 15 can produce corresponding bore holes for the bone screws which are to be placed into the bores 4.

Figure 5:
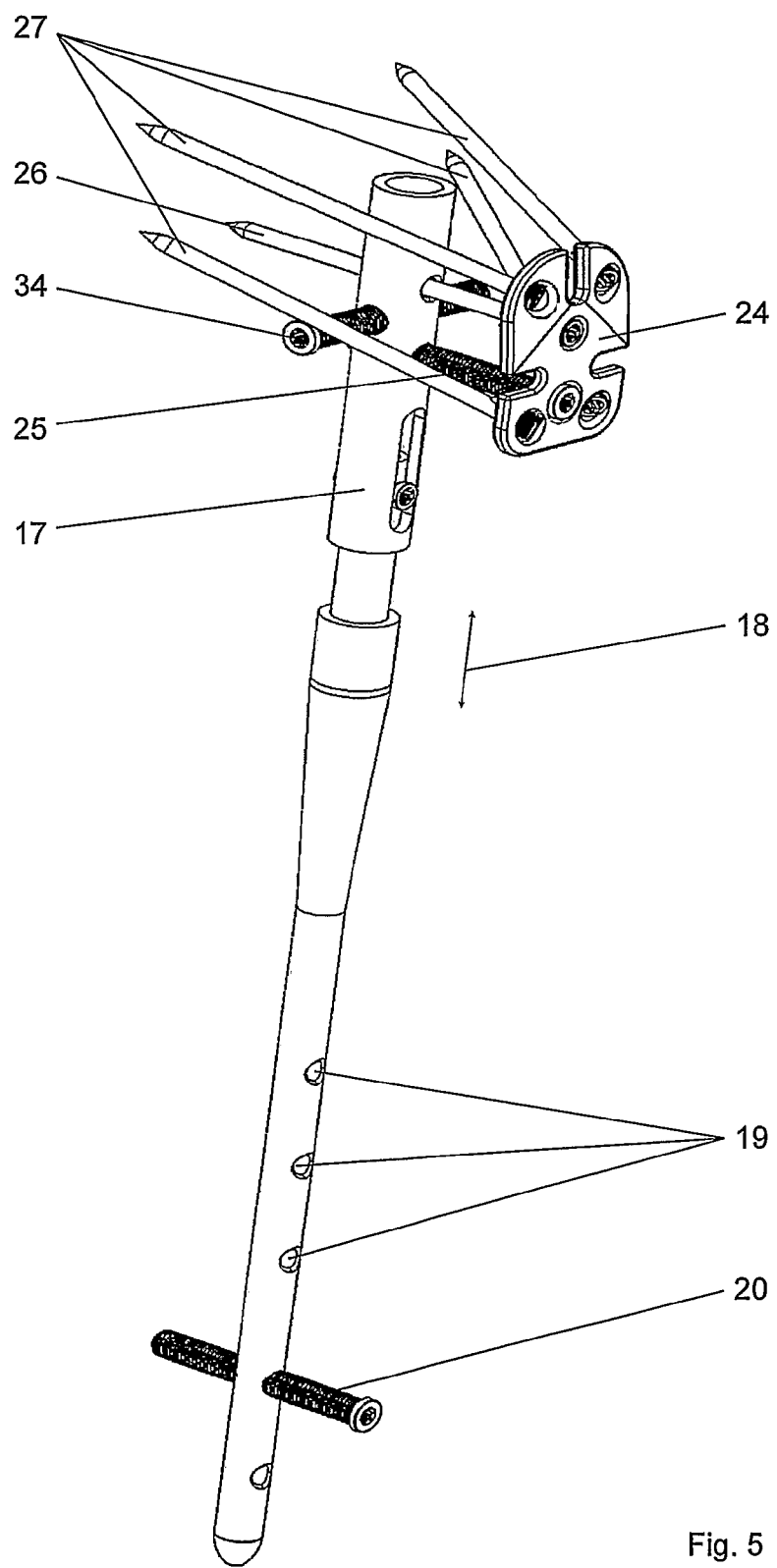
FIG. 5 is a second embodiment of the implant according to the invention.

In FIG. 5 a second embodiment of the implant according to the invention is illustrated. The implant consists again of a distal part 16 and a proximal part 17, which are freely displaceable relative to each other in an axial direction according to the double arrow 18. The distal part 16 has a plurality of bores 19, which serve to receive fixing means and in particular bone screws. By way of example, a bone screw 20 is illustrated. The proximal part 17 has bores 21, 22 and 23 (FIG. 7), which likewise serve to receive or fasten fixing means. In the present case, a plate 24 is provided, which is intended to rest areally on the bone surface and is thereby intended to stabilize the bone debris. The plate 24 is fastened by means of a fixing screw 25 and a post 26 on the proximal part 17. Furthermore, a plurality of posts 27 are fastened in an angle-stable manner in the plate 24, in order to stabilize bone fragments. Further details of the construction according to FIG. 5 can be seen from the following description of FIGS. 6 to 10.

Figure 6:
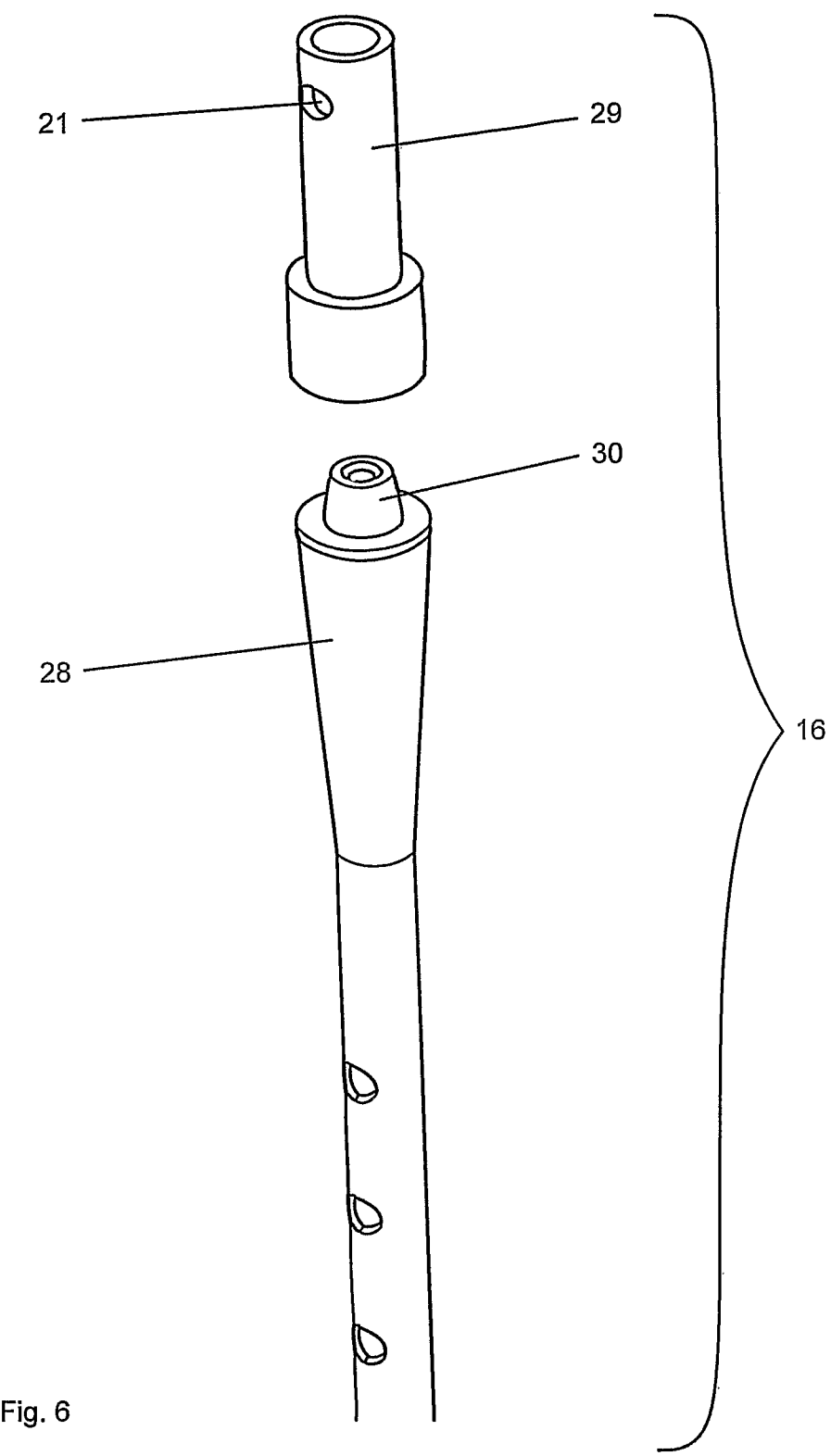
FIG. 6 is a view of the distal part of the implant of FIG. 5 in pulled-apart illustration.

In FIG. 6 it can be seen that the distal part 16 is composed of a base part 28 and an intermediate piece 29. In order to ensure a stable connection of the base part 28 with the intermediate piece 29, the base part 28 has an extension 30 in the shape of a truncated cone, which is received, substantially free of play, into a corresponding cavity, in the shape of a truncated cone, of the intermediate piece 29. For the axial fastening of the intermediate piece 29 on the base part 28, a fastening screw, which is not illustrated in further detail, is provided which is introduced into the hollow cross-section of the intermediate piece 29 and is screwed into the extension 30.

The two-part construction of the distal part 16 is provided in order to facilitate, if necessary, the fastening of a prosthesis. For this purpose, the intermediate piece 29 is removed and the base part 28 serves as a prosthesis shaft for a prosthesis, such as for example a humerus head prosthesis.

Figure 7:
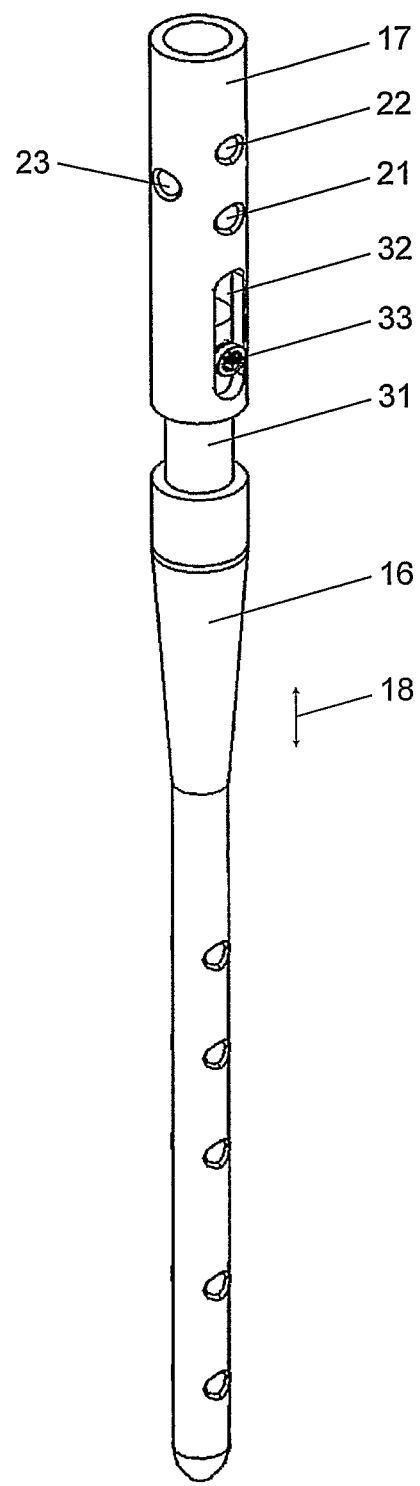
FIG. 7 is an illustration of the reciprocal displaceability of the distal and of the proximal part in an implant according to FIG. 5.

In FIG. 7 it is illustrated how the distal part 16 and the proximal part 17 are guided so as to be displaceable relative to each other. For this purpose, the distal part 16 has a cylindrical region 31 with a reduced diameter, which is guided in a corresponding cavity of the proximal part 17 in the direction of the double arrow 18. In order to prevent the relative rotation of the two parts about the implant axis, the proximal part 17 has an elongated hole 32, which is penetrated by a bolt 33 which is fastened on the distal part 16. The bolt 33 permits an axial displacement of the two parts 16 and 17 relative to each other, but prevents a rotation of the two parts 16 and 17 relative to each other about the implant axis. At the same time, the bolt 13 forms a stop for delimiting the relative displacement of the two parts 16 and 17.

In FIG. 7 it can be further seen that the proximal part 17 has two bores 21 and 22, which serve to receive fixing means and in particular a bone screw or respectively a post, in order to fasten the plate 24 on the proximal part 17, as is explained in further detail below with the aid of FIGS. 8 and 10. Furthermore, the distal part 17 has a further bore 23, which runs transversely to the bores 21 and 22. The bore 23 serves to receive a bone screw 34, by which bone fragments can be fixed.

Figure 8:
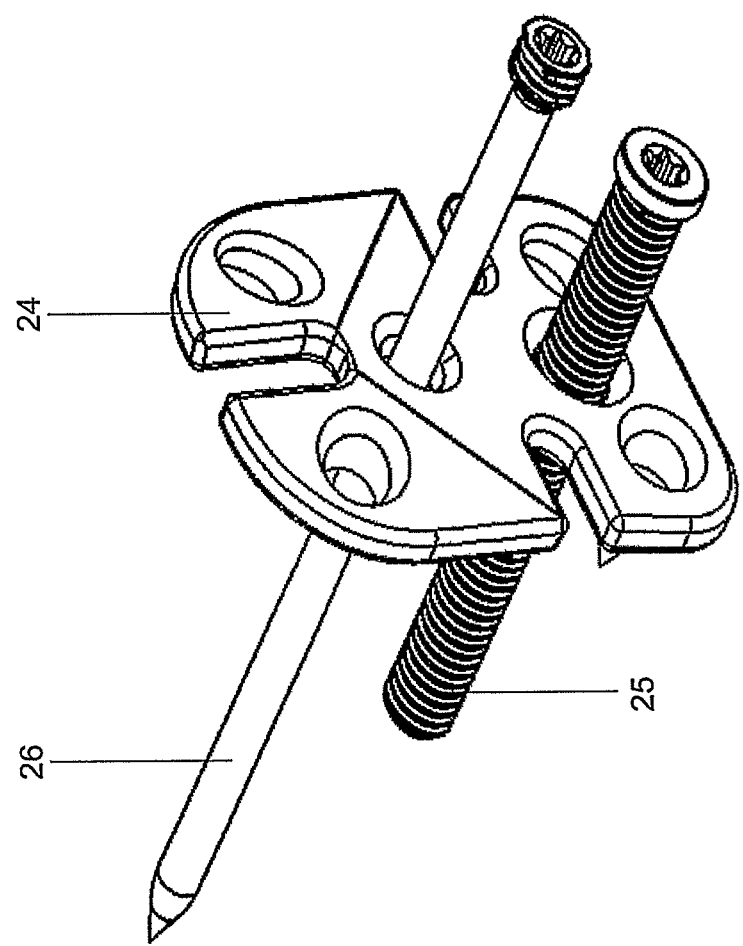
FIG. 8 is a detail view of the plate provided in the implant according to FIG. 5.
Figure 10:
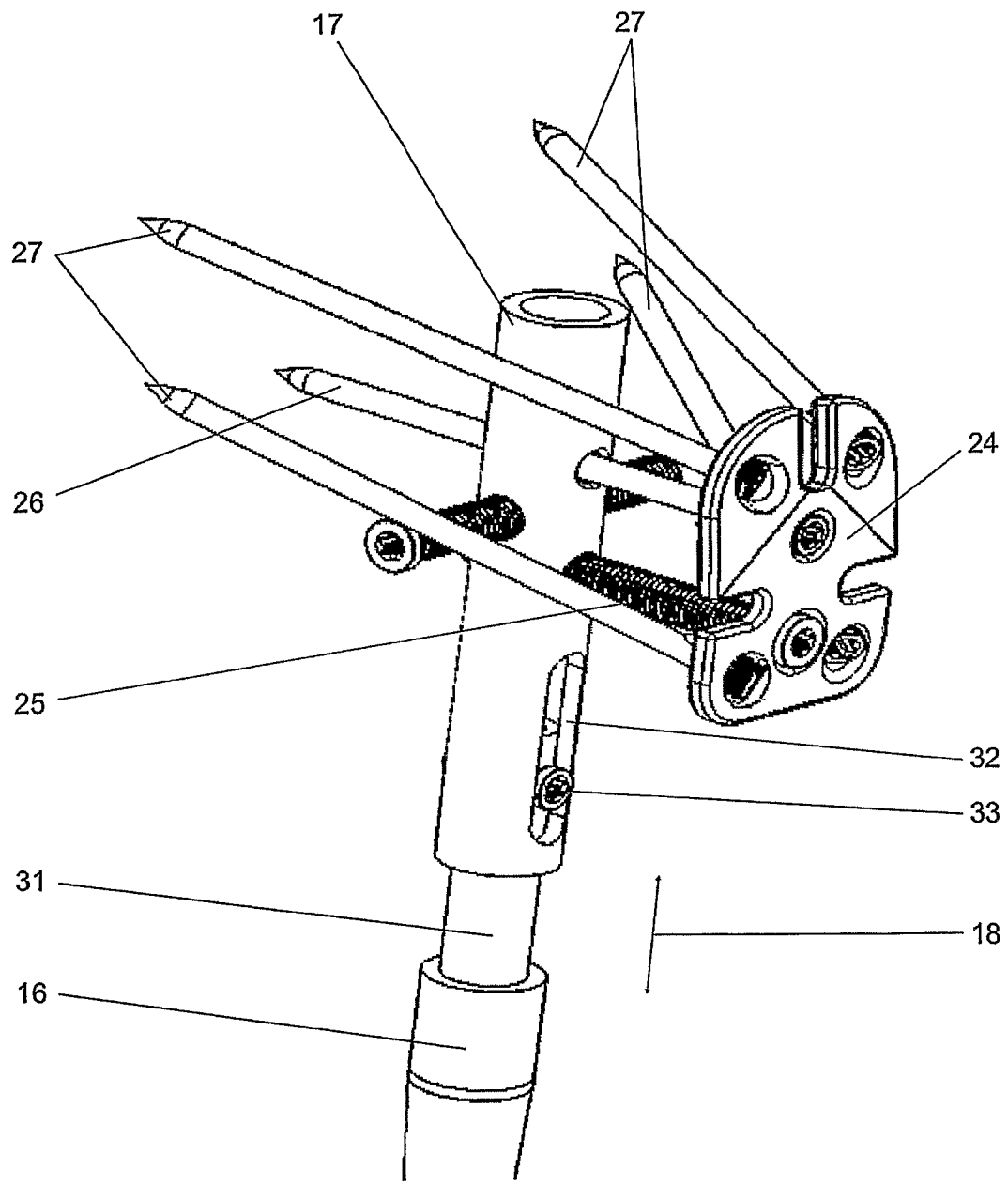
FIG. 10 is a detail view of the proximal part with a plate fastened thereon.

From viewing FIG. 8 together with FIG. 10, it can be seen how the plate 24 is fastened on the proximal part 17. A bone screw 25 is provided, which is introduced via a bore in the plate 24 and is screwed into a pre-drilled hole in the bone, until it subsequently penetrates into the bore 21 of the proximal part 17 and is screwed in there by means of its thread. The screw head of the bone screw 25 forms a stop which cooperates with the plate 24, so that the plate 24, on screwing in of the bone screw 25 into the internal thread of the bore 21, is drawn in the direction to the proximal part 17. The surgeon draws the plate 24 here in the direction to the distal part 17 until the plate 24 rests against the bone. The screw head of the screw 25 is constructed here so that a pivoting of the screw 25 relative to the plate 24 is made possible, so that the plate 24 can apply itself exactly onto the bone.

The plate 24 is subsequently secured against rotation by means of the post 26. Here, the post 26 has a head which is provided with a thread, which cooperates with the corresponding bore in the plate 24, so that an angle-stable connection of the post 26 with the plate 24 is achieved. Thereby, the plate 24 is fixed in the respective position. The post 26 does not have a thread on its shaft here, whereby it is made possible that the post 26 is initially driven into the bone in an axial direction, and subsequently can penetrate into the bore 22 in the proximal part 17. Only when the screw head reaches the associated bore of the plate 24 is the post 26 fixed in an angle-stable manner with a few turns in the plate 24. Through the fact that the post 26 initially, however, can be exclusively driven home by driving in in an axial direction, a precisely targeted introduction of the post is ensured, without the deviations from the introduction direction ("wavering") occurring, which are usually to be observed on screwing in.

The further fixing posts 27 are introduced in an identical manner to the post 26. The head of the posts 27, which is provided with a thread, is constructed here such that within certain limits a choice can be made of the angle between post 27 and the plane of the plate 24. In the selected angle, an angle-stable fixing of the post 27 then takes place in the plate 24. It is thereby made possible in a simple manner for the surgeon to introduce the fixing posts 27 in an optimum direction for the stabilizing of the individual bone fragments.

Figure 9:
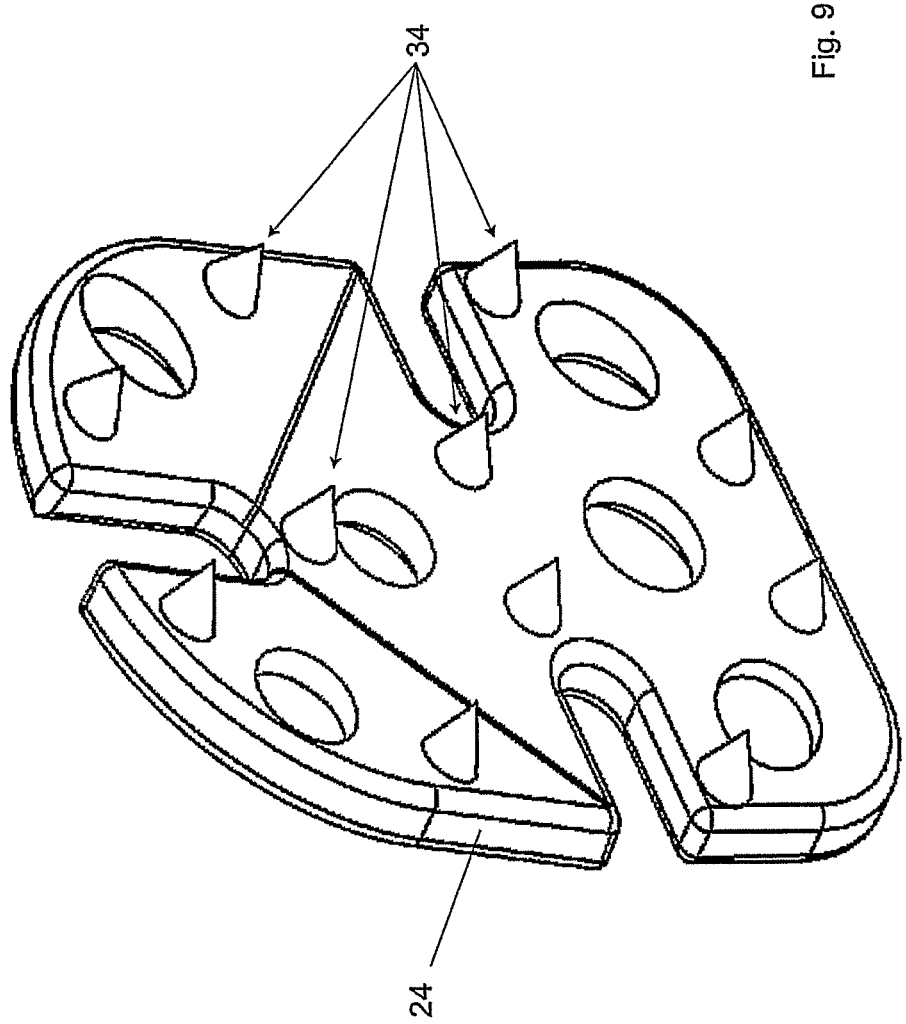
FIG. 9 is a view of the underside of the plate.

In FIG. 9 it can be seen that the surface of the plate 24 facing the bone has a plurality of projecting points 34, which lead to the plate 24 resting on the bone merely with the points 34. The projecting points offer a good hold here on the bone fragments, but at the same time lead to the plate 24 not resting with its entire surface on the bone, so that periosteal compression is avoided.

The invention claimed is:

1. Implant for treating a proximal fracture of the humerus, with at least one distal and at least one proximal part which are arranged so as to be displaceable axially relative to each other to modify the length of the implant and have guide surfaces cooperating with each other, characterized in that the distal and the proximal part have stops cooperating with each other for limiting the axial relative displacement, that the distal and the proximal part are freely displaceable relative to each other within the delimitations defined by the stops, that the proximal and the distal part are respectively provided with at least one transverse bore for receiving and/or fastening fixing means, and that means are provided for locking the relative twisting of the two parts about the implant axis, and wherein the guide surfaces respectively have at least one groove running in an axial direction, in the shared cross-section of which a rod is received.

2. Implant according to claim 1, characterized in that at least one bone screw is provided as fixing means.

3. Implant according to claim 1, characterized in that the proximal part has at least two intersecting transverse bores.

4. Implant according to claim 1, characterized in that the guide surfaces are constructed so as to be cylindrical in sections.

5. Implant according to claim 1, characterized in that the guide surfaces form a cross-section of the implant deviating from a circular cross-section.

6. Implant according to claim 1, characterized in that the proximal or the distal part has an elongated hole extending in an axial direction, in which a bolt, arranged on the other part so as to be secure with regard to rotation, is guided in an axial direction.

7. Implant according to claim 1, characterized in that a plate is provided as fixing means, which is able to be fastened relative to the proximal part of the implant.

8. Implant according to claim 7, characterized in that for fastening the plate at least one screw is provided, which connects the plate with the proximal part of the implant.

9. Implant according to claim 8, characterized in that in addition to the screw, a post is provided for connecting the plate with the implant, the screw head of which has a thread for screwing into the plate and the end of which, facing away from the screw head, is able to be introduced into a threadless transverse bore of the implant.

10. Implant according to claim 7, characterized in that the plate has a plurality of through-holes to receive fixing screws and/or posts for the fixing of bone fragments.

11. Implant according to claim 7, characterized in that for the fixing of bone fragments, posts and/or fixing screws are provided, which are able to be fastened in an angle-stable manner in the plate.

12. Implant according to claim 1 and target device for the placing of bone screws in transverse bores of the implant, characterized in that the target device has two parts which are displaceable relative to each other in an axial direction, one part of which is able to be connected with the proximal or the distal part of the implant and together therewith is able to be displaced relative to the other part.

13. Implant and target device according to claim 12, characterized in that the one part of the target device is formed by a sleeve, able to be pushed over the proximal implant part, which sleeve rests on a projection of the distal implant part, and the other part of the target device is formed by a rod arranged in the sleeve, which rod is able to be connected with the proximal implant part preferably by means of a screw connection.

14. Implant and target device according to claim 12, characterized in that the rod carries at its proximal end a screw nut, which rests, if applicable indirectly, against the sleeve of the target device.

15. A method of treating a proximal fracture of a humerus, comprising the step of utilizing the distal part of an implant according to claim 1, as a prosthesis shaft for a humerus head prosthesis.

16. The method according to claim 15, further comprising the step of utilizing an intermediate piece for adjusting the vertical and rotation position and for securing the humerus prosthesis, wherein the intermediate piece is fastened on the distal part of the implant.

* * * * *

UNITED STATES PATENT AND TRADEMARK OFFICE
CERTIFICATE OF CORRECTION

PATENT NO. : 8,486,072 B2
APPLICATION NO. : 13/063157
DATED : July 16, 2013
INVENTOR(S) : Christian Haininger It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 173 days.

Signed and Sealed this
Eighth Day of September, 2015

Michelle K. Lee
*Director of the United States Patent and Trademark Office*